United States Patent [19]

Kurata et al.

[11] 3,959,389

[45] May 25, 1976

[54] METHOD OF MANUFACTURING ALKYLENE OXIDE ADDUCTS OF AN ALIPHATIC ALCOHOL

[75] Inventors: Naoji Kurata, Nishinomiya; Kazuo Koshida, Ashiya; Toshihiro Fujii, Moriguchi; Koichi Matsuhiro, Achiya; Yukio Okuda, Toyonaka, all of Japan

[73] Assignee: Nippon Shokubai Kagaku Kogyo Co., Ltd., Osaka, Japan

[22] Filed: Feb. 1, 1974

[21] Appl. No.: 438,531

Related U.S. Application Data

[62] Division of Ser. No. 271,685, July 14, 1972.

[52] U.S. Cl. .................. 260/615 B; 260/615 R; 260/639 B; 260/643 A
[51] Int. Cl.² .................. C07C 41/02; C07C 41/10
[58] Field of Search ........ 260/615 B, 639 B, 643 A, 260/615 R

[56] References Cited
UNITED STATES PATENTS

| | | | |
|---|---|---|---|
| 2,587,753 | 3/1952 | O'Connor et al. | 260/639 B |
| 2,870,220 | 1/1959 | Carter | 260/615 B |
| 2,885,446 | 5/1959 | Sharp et al. | 260/643 A |
| 3,281,477 | 10/1966 | Nielsen | 260/615 B |
| 3,346,614 | 10/1967 | Starks et al. | 260/639 B |
| 3,372,201 | 3/1968 | Leary et al. | 260/615 B |
| 3,442,959 | 5/1969 | Sugerman | 260/639 B |
| 3,524,891 | 8/1970 | Cahn | 260/639 B X |
| 3,524,893 | 8/1970 | Doyle et al. | 260/639 B |
| 3,558,687 | 1/1971 | Russel | 260/639 B |

FOREIGN PATENTS OR APPLICATIONS

| | | | |
|---|---|---|---|
| 534,884 | 12/1956 | Canada | 260/643 A |
| 1,919,593 | 12/1969 | Germany | 260/639 B |
| 1,097,152 | 12/1967 | United Kingdom | 260/643 A |

*Primary Examiner*—Howard T. Mars
*Attorney, Agent, or Firm*—Armstrong, Nikaido & Wegner

[57] ABSTRACT

An improvement is provided in the manufacture of alkylene oxide adducts of an aliphatic alcohol in which the reaction mixture, comprising the alkylene oxide adduct, unreacted alcohol, acid catalyst residue, carbonyl compounds and hydrocarbons, is treated to remove unreacted alcohol for recycle to the adduct formation step. To prevent the build-up in the system of carbonyl compounds and hydrocarbons which are not easily distillable from the recycle alcohol because of their respective boiling points, at least a portion of the recycle alcohol is esterified with boric acid, the esterification mixture is subjected to distillation to remove volatile portions, and the borate ester thus obtained is hydrolyzed to recover the alcohol which is recycled to the adduct formation step.

8 Claims, 3 Drawing Figures

METHOD OF MANUFACTURING ALKYLENE OXIDE ADDUCTS OF AN ALIPHATIC ALCOHOL

This is a division of application Ser. No. 271,685 filed July 14, 1972.

BACKGROUND OF THE INVENTION

This invention relates to an improved method of manufacturing alkylene oxide adducts of an aliphatic alcohol, said alcohol having been obtained by the liquid phase oxidation of a saturated aliphalic hydrocarbon having 8 to 20 carbon atoms in the presence of a boron compound by contacting with a molecular oxygen containing gas.

In the addition reaction of alkylene oxides to alcohols in the presence of an acid catalyst, it is known that the conversion of alcohols must be to an extent of 30 to 80 % from the economic point of view, so that it is necessary to recover unreacted alcohols by means of, e.g., distillation, and to recycle the recovered alcohols to the reaction system.

Not only alcohols obtained by the oxidation of hydrocarbons but alcohols in general may contain impurities, e.g. carbonyl compounds and hydrocarbons, which do not react with alkylene oxide. Such impurities are accumulated in the system with the recycle of recovered alcohols and this makes it difficult to obtain a product of a uniform quality by continuing the reaction under the same conditions. As the reaction is continued or repeated, the content of the impurities gradually increases and, with this, the average number of moles of added alkylene oxide (it will hereinafter be referred to as $\bar{n}$.) per mole of alcohol in the product gradually varies. Therefore, it is necessary in order to obtain a product of a uniform quality to continually adjust the feed rate of fresh alcohol and/or alkylene oxide and to vary the material balance in the separation step of unreacted alcohol and of impurities by means of, e.g., distillation. Unfortunately, it is difficult to completely separate the impurities, because of the relationship of their boiling points to that of the alcohol and the accumulated impurities at last make it impractical to recycle the recovered alcohol.

If the impurities contained in raw alcohols are simple carbonyl compounds or olefinic compounds hydrotreating may be employed in the purification step. Such a treatment has been utylyzed in practical to improve color and odor of the products but is ineffective for the complete removal of impurities contained in raw alcohols, e.g. hydrocarbons.

Therefore, there is a need for an improved method of manufacturing alkylene oxide adducts of aliphatic alcohols having uniform good quality in which removal of accumulated impurities is attained economically and efficiently.

An object of the present invention is to provide an improved method of manufacturing alkylene oxide adducts of aliphatic alcohols having uniform good quality in which removal of accumulated impurities is attained economically and effectively.

SUMMARY OF THE INVENTION

An improvement is provided in the manufacture of alkylene oxide adducts of an aliphatic alcohol in which a saturated aliphatic alcohol having 8 to 20 carbon atoms is subjected to the reaction with an alkylene oxide having 2 to 4 carbon atoms in the presence of an acid catalyst and unreacted alcohol containing impurities comprising hydrocarbons and carbonyl compounds are separated from the reaction mixture. The improvement comprises;

a. subjecting at least a portion of said unreacted alcohol to esterification with a boric acid to form a borate ester of said alcohol,
b. removing said impurities from the esterification mixture,
c. subjecting the borate ester thus obtained to hydrolysis to recover the alcohol and
d. recycling the recovered alcohol to the adduct formation step.

DETAILED DESCRIPTION OF THE INVENTION

In accordance with the present invention, alkylene oxide adducts of aliphatic alcohols having uniform good quality are produced from an aliphatic alcohol having from 8 to 20 carbon atoms per molecule and containing impurities which do not react with alkylene oxide. Said adducts are obtained by (1) subjecting said alcohol to reaction with pre-determined amount of an alkylene oxide in the presence of acid catalyst (this step will hereinafter be referred to, for short, as "alkoxylation".), (2) recovering unreacted alcohol by means of, e.g., distillation, from the reaction mixture, if necessary after removal of the catalyst and some by-products, formed in the alkoxylation, (3) reacting a portion or all of the recovered alcohol with a boric acid, (4) separating the resulting boric acid ester from the impurities, (5) hydrolyzing the separated borate ester to liberate the alcohol, and (6) recycling the alcohol thus obtained to the alkoxylation step, if necessary after removal of moisture, in combination with the other portion of the recovered alcohol which is not subjected to the esterification reaction.

In the above process, the concentration of impurities in the recycled alcohol increases with continuation of the operation to a certain value but thereafter becomes constant. Therefore the impurities contained in the raw material do not cause such troubles as mentioned above in connection with the prior art and, consequently, there is obtained a product of uniform good quality economically and continuously, because the alkoxylation reaction and the recovering unreacted alcohol can be conducted uniformly.

In addition, in accordance with the present invention, it is possible to produce commercially and continuously alkylene oxide adducts of alcohols having uniform good quality by using the above process in combination with the oxidation process of saturated aliphatic hydrocarbons to alcohols. To say, the method of the present invention makes it possible to produce directly alkylene oxide adducts of saturated aliphatic alcohols directly advantageously from aliphatic hydrocarbons without any particular unit process, effectively utilizing the impurities contained in said alcohols, which have hithereto been discarded.

Figure 1:
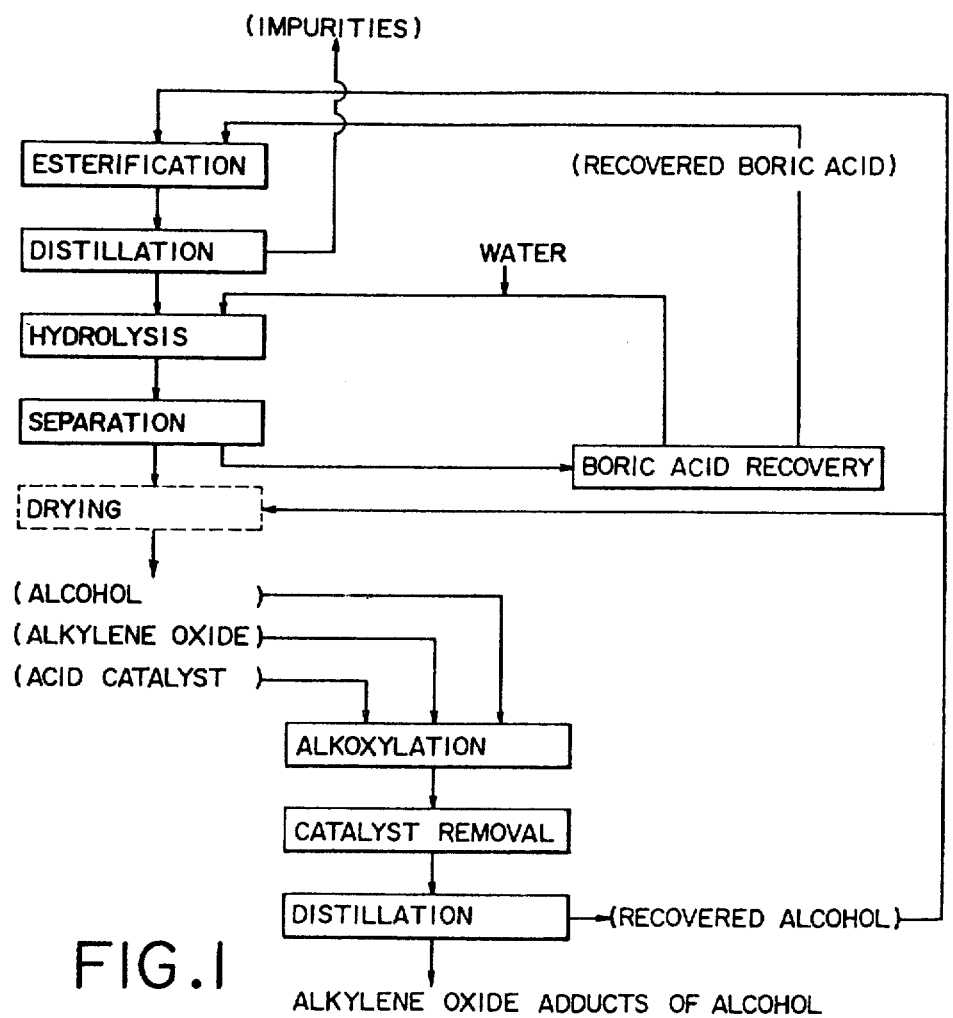
Figure 2:
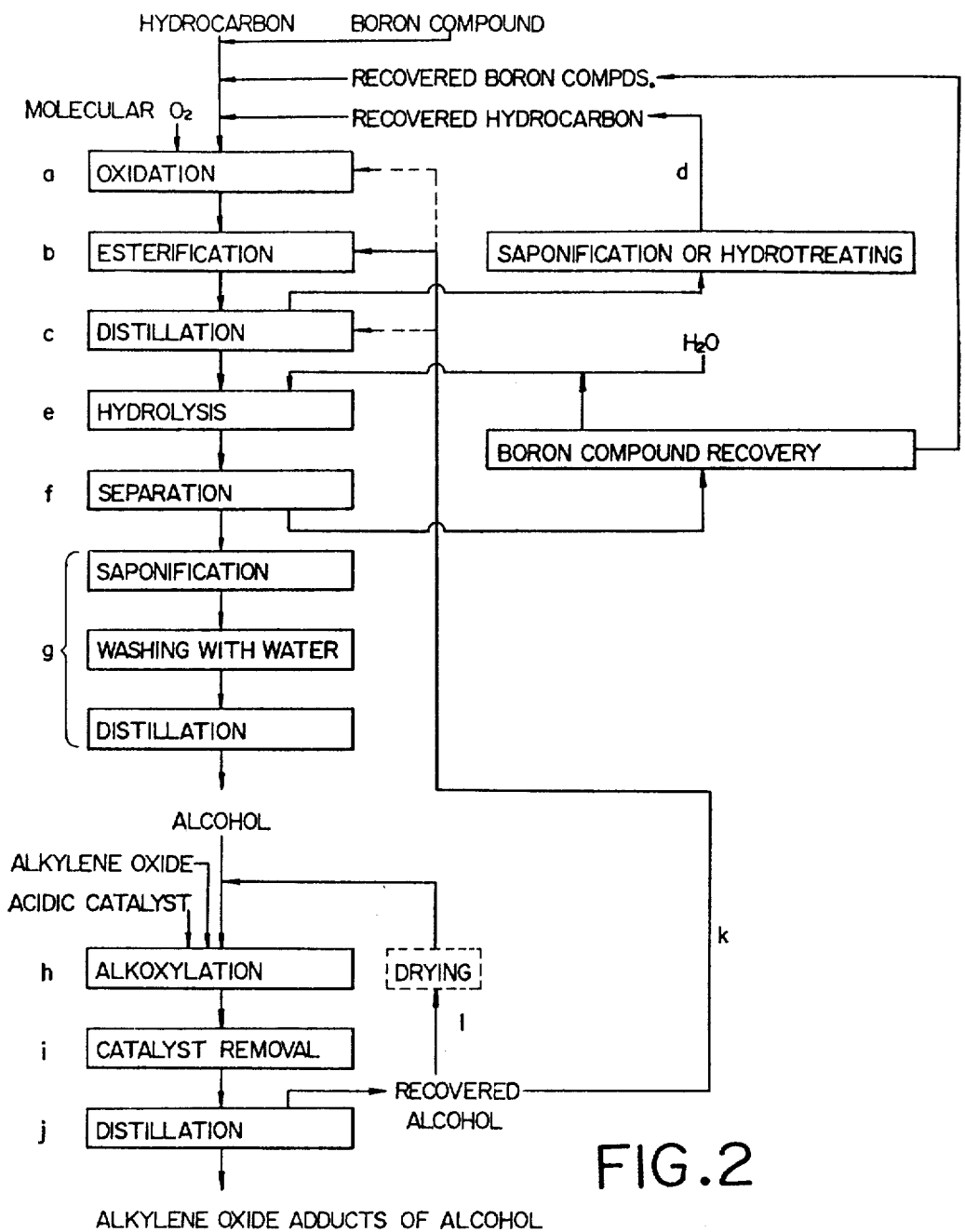
Figure 3:
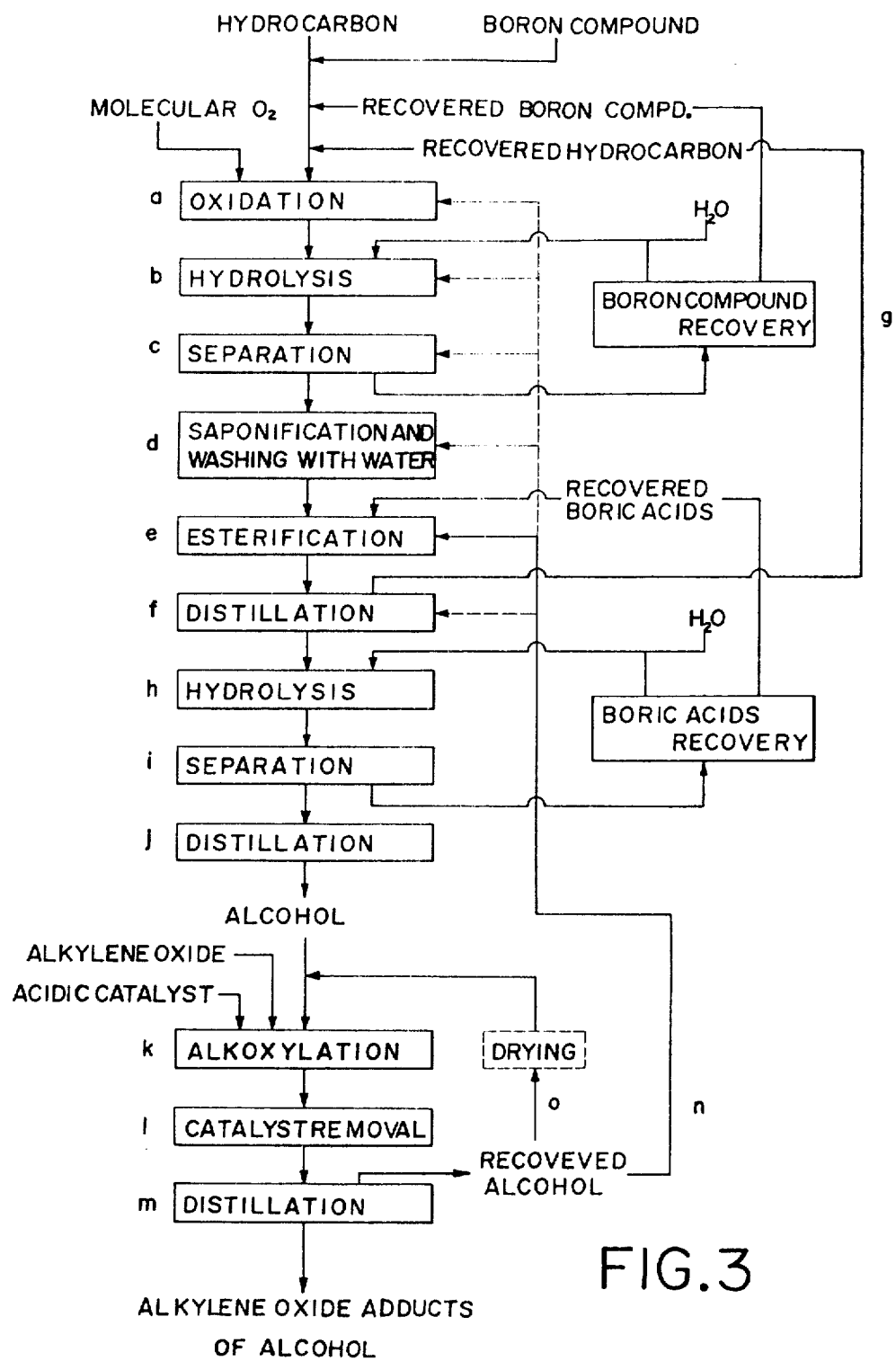

The present invention will be understood best in connection with the accompanying drawings wherein;

FIG. 1 is a flow diagram illustrating the fundamental of the method of manufacturing alkylene oxide adducts of aliphatic alcohols in accordance with the present invention, FIG. 2 is a flow diagram illustrating an embodiment of the process of the present invention in combination with the manufacture of the alcohol, and FIG. 3 is a flow diagram illustrating another embodiment of the process of the present invention in combination with the manufacture of the alcohol.

Illustrating the present invention with respect to FIG. 1, in alkoxylation step there are added to the alcohol an acid catalyst and an alkylene oxide. The starting alcohol can be any saturated aliphatic alcohol having 8 to 20 carbon atoms per molecule. In general, alcohols obtained by liquid phase oxidation of straight chain saturated aliphatic hydrocarbons having 8 to 20 carbon atoms per molecule by molecular oxygen containing gas in the presence of a boron compounds are conveniently used as such. As the alkylene oxide there are used those containing 2 to 4 carbon atoms per molecule, the preferred ones being ethylene oxide and propylene oxide. Mixtures of two or more of such alkylene oxides can also be used. As the acid catalyst there can be used mineral acids such as sulfuric acid and phsphoric acid, or Lewis acids or Friedel-Crafts catalysts. Among such acid catalysts, the most suitable are boron trifluoride and its complexes with, e.g., methanol, ethanol, isopropanol, butanols, ethylether, n-butylether, phenylether, acetic acid, propionic acid, phenol, monomethylamine, monoethylamine, dimethylamine, triethylamine or piperidine, tin chlorides and antimony chlorides.

The mole ratio of alcohol to alkylene oxide fed to the reaction zone for alkoxylation, although it varies in accordance with the $\bar{n}$ of the end product, is 0.5 to 4, preferably 0.8 to 2.0 since the $\bar{n}$ is usually restricted to 1 to 6 by the nature of the acid catalysted alkoxylation. The acid catalyst is usually used in an amount of 0.01 to 1 %, preferably 0.05 to 0.5 % by weight based on the weight of the alcohol.

The reaction may be conducted in either a batchwise operation or a continuous operation. In the case of a batchwise operation, it is convenient to charge first the alcohol and the catalyst to a stirred reaction vessel and then add slowly thereto the alkylene oxide.

In case of the continuous operation, it is convenient to pass the catalyst containing-alcohol through a tubular reactor while adding thereto the alkylene oxide from two or more inlets positioned in the wall of the tubular reactor. The temperature, pressure, reaction time and other conditions can be properly selected depending on the kind and amounts of raw alcohol, alkylene oxide and catalyst used. Usually, the reaction temperature will be properly selected from the range between room temperature (20°C) and 100°C.

After the alkoxylation, if desired, the catalyst and by-products are removed from the reaction mixture. The catalyst can be removed by neutralization and subsequent filteration of the reaction mixture or by extraction with water. Among the by-products of alkoxylation, water-soluble polyalkylene glycols and dioxanes can be removed by extraction with water.

Distillation is the most convenient means for the recovery of unreacted alcohol; the alkylene oxide-alcohol adduct being recovered as the residue. The recovered alcohol is in whole or in part subjected to esterification with a boric acid. Althought the larger the proportion of recovered alcohols subjected to the esterification, the higher the quality of the end product, it is preferred to subject 1 to 50 % of recovered alcohol to the esterification from a commercial point of view. In the case where unreacted alcohols is recovered by distillation, the objects of the present invention are attainable more efficiently by subjecting to esterification a forerun amounting to 1 to 20 % of the entire distillate to the esterification. In Example II hereinafter set forth the recovered alcohol was processed in this manner, and the advantage is apparent from the comparison of the result in Example II with that of Example I and of Comparative Example I.

The boric acids used in the esterification include orthoboric acid, metaboric acid, pyroboric acid and boric acid anhydride, although is preferably used orthoboric acid. The boric acid can be used in an amount, such as to provide 0.3 to 3, preferably 0.4 to 1.5 gram-atoms of boron atom per mole of alcohol.

The esterification usually is carried out using a stirred reaction vessel at temperatures of 100° to 200°C under a reduced pressure or in an atmosphere of an inert gas such as gaseous nitrogen with immediate removal of liberated water when water is liberated as a result of esterification. Usually a reaction time of 10 to 100 minutes is sufficient.

Separation of impurities from the esterification product is conveniently attained by an ordinary distillation. The impurities are removed as distillate and the boric acid ester of the alcohol is recovered as residue. The distillation preferably is conducted under reduced pressure to minimize thermal decomposition of the product and a still better result is obtained by use of a thin film evaporator because of a shorter residence time. The distillation may be conducted in the presence of an inert solvent of a lower boiling point than the impurities in order to aid effluence of the impurities. The distillate contains impurities which originate from the raw alcohol and remain unreacted during alkoxylation, such impurities generally comprising hydrocarbons and carbonyl compounds. Although the impurities are in most cases discarded, there are good uses therefor as illustrated hereinafter in connection with FIG. 2 and FIG. 3.

The boric acid esters thus obtained as residue in the distillation kettle is then hydrolysed. The hydrolysis may be carried out in various ways, e.g. in a batch operation using a stirred tank, or in a continuous operation or by means of a counter-current extractor. Water preferably is used in a weight ratio to the residue of 10:1 to 1:10. The temperature can be varied within the range from room temperature (20°C) to 200°C. Sometime, it is advantageous to carry out the hydrolysis at temperatures above 100°C under pressure.

The alcohol yielded in the hydrolysis is separated as an oily layer from the aqueous boric acid solution. From the squeous boric acid solution is recovered boric acid which is then recycled to the esterification step while the mother liquor from the recovery of boric acid is recycled to the hydrolysis step.

The alcohol thus obtained is combined with the remainder of recovered alcohols which has not been subjected to esterification and, after removal of moisture if required, recycled to the alkoxylation step.

As mentioned above, in the method of the present invention, impurities of the same or similar boiling points as those of the recovered alcohol are substantially completely eliminated as a low boiling fraction during the distillation, because the unreacted alcohol fraction separated from the alkoxylation mixture after completion of the reaction is, in whole or in part, subjected to esterification with a boric acid and then to distillation to separate the recovered alcohol as residue in the form of a boric acid ester. Thus, impurities can be eliminated to the extent desired during purification of the recovered alcohol, so that the purity of the alcohol recycled to the alkoxylation stage becomes constant.

This makes it possible to continuously produce alkylene oxide adducts of aliphatic alcohols having uniform good quality without any adjustment of reaction conditions for the alkoxylation and conditions for recovery of unreacted alcohol. Example I and Comparative Example I are provided for the purpose of the simplest comparison of the method of the present invention with a conventional method. The superiority of the method of the present invention will be easily understood by the comparison.

It is more advantageous to combine the method of the present invention with the preparation of aliphatic alcohols by liquid phase oxidation with a molecular oxygen containing gas of corresponding straight chain saturated aliphatic hydrocarbons having 8 to 20 carbon atoms per molecule in the presence of a boron compound. Any aliphatic hydrocarbon having 8 to 20 carbon atoms can be subjected to oxidation, though conveniently used are n-octane, n-nonane, n-decane, n-undecane, n-dodecane, n-tridecane, n-tetradecane, n-pentadecane, n-hexadecane, n-heptadecane and n-octadecane. Mixtures of two or more of such hydrocarbons having 10 to 16 carbon atoms are suitably used in commercial operation.

As the boron compound there may be used, other than boric acids, any of boron compounds which will yield boric acids upon contact with water. Preferred compounds are orthoboric acid, metaboric acid, boric anhydride, salts thereof, borate esters and boroxines.

The flow diagrams of FIG. 2 and FIG. 3 illustrate such combinations. Illustrating in more detail with reference to FIG. 2, in oxidation stage (a), an aliphatic hydrocarbon is oxidized in liquid state in the presence of 1 to 5 % by weight, caluculated as metaboric acid, based on the weight of the hydrocarbon of a boron compound with a molecular oxygen containing gas containing 2 to 21 % by volume of molecular oxygen in an inert gas such as gaseous nitrogen, at temperatures of 140° to 200°C, preferably 150° to 190°C. The conversion of the hydrocarbons is usually restricted to at most 30 %, preferably 10 % to 20 %, in order to obtain the alcohol in a high yield. The reaction time can range from 0.5 to 4 hours, preferably from 1 to 3 hours. In esterification step (b), the oxidation mixture is maintained usually at a temperature of 100° to 200°C, preferably at a temperature in the neighbourhood of the oxidation temperature under reduced pressure or in an atmosphere of an inert gas for 10 to 100 minutes. The esterification step is employed for conversion of a portion of the recovered alcohol recycled from the alkoxylation stage in addition to completion of esterification of the oxidation product. When the boron compound is present insufficiently in the system, it may be added in the stage to the system. In the following distillation step (c), unreacted hydrocarbon is distilled off together with volatile by-products. The distillation preferably is carried out at a temperature as low as possible and, accordingly, under reduced pressure. It is favorable to carry out the distillation in two stages to shorten the residence time of the effluent and to conduct the second stage in a thin film evaporator. The distillate is recycled to the oxidation step, preferably after the purity of hydrocarbons in the distillate has been increased by saponification or hydrotreating (d).

Hydrolysis (e) of the boric acid ester of the alcohol obtained as residue is performed in a similar manner as in the description of the process illustrated in FIG. 1. In separation step (f), boric acid is recovered from the aqueous solution separated to the preceeding hydrolysis step (e) by crystallization and, after dehydration if required, recycled to the oxidation step, while the mother liquor may be recycled to the hydrolysis step for economization of the process.

The crude alcohol separated as an oily layer in the hydrolysis step is then purified (g) in various ways. For instance, it is purified usually by means of distillation following such post treatments as, e.g., saponification by contact with an alkali hydroxide, such as potassium hydroxide or sodium hydroxide, washing with water, hydrotreating by contact with hydrogen in the presence of a metallic catalyst. The purification method consisting of the steps of saponification, washing with water and distillation, combined in this order, as indicated in FIG. 2 is just by way of example and, of course, this purificating may be carried out using other variations.

Alkoxylation step (h), catalyst removal (i) and distillation (j) are carried out in the same ways as explained in connection with FIG. 1.

The recovered alcohols obtained in the distillation of the product of step (j) may be recycled (k) in whole or in part to either oxidation step (a), esterification step (b) or distillation step (c), though it is particularly desirable for avoidance of undesirable side reactions of the recovered alcohol and completion of esterification to recycle it to esterification step (b). In the case of a process in which the esterification step (b) is omitted, the alcohol may be recycled to the oxidation step (e) or distillation step (c). The balance of recovered alcohol unrecycled to the oxidation step (a), (a), esterification step (b) or distillation step (c) is recycled, if necessary after dehydration or drying (1), to the alkoxylation step. A better result is obtainable by recycling the forerun from the distillation (j) to the esterification step (b) and the other fractions to the alkoxylation step (h).

In accordance with the process as shown in FIG. 2, there is continuously produced from a hydrocarbon as mentioned above an alkylene oxide adduct of a corresponding alcohol having uniform good quality in a high yeild without careful adjustment of conditions for alkoxylation and distillation. This process will be illustrated specifically in Example III.

The process as shown in FIG. 3 is a modification of the process as shown in FIG. 2. After liquid phase oxidation (a) of a hydrocarbon in the presence of a boron compound in a similar manner as explained in connection with in FIG. 2, the reaction mixture is directly subjected to hydrolysis. The hydrolysis (b) may be carried out in various ways in the same manner as the hydrolysis (e) in the process of FIG. 2. The aqueous boric acid solution thus formed is separated (c) and from the solution is recovered boric acid by crystallization which in turn is recycled after dehydration if required to the oxidation step, while the mother liquor is recycled to the hydrolysis step (b). The organic layer obtained is saponified by contact with an alkali hydroxide, such as potassium hydroxide, sodium hydroxide or lithium hydroxide, and washed with water (d). The saponification preferably is conducted at temperatures of 100° to 200°C for few minutes to several hours using an aqueous alkali hydroxide solution of a concentration of 1 to 50 % by weight.

The esterification in esterification step (e) is carried out under the same conditions as explained in connection with the esterification in the process of FIG. 1. In distillation step (f), unreacted hydrocarbon is separated in a similar way as in the distillation step (c) in FIG. 2, and the distillate (g) is recycled to the oxidation step (a). Hydrolysis step (h) and separation (i) correspond to the hydrolysis step (e) and separation (f) in FIG. 2 are conducted in a similar manner. Recovery and recycle of boric acid and recycle of the mother liquor from the recovery of boric acid are also carried out in a similar manner.

Purification (j) of crude alcohol is performed by means of distillation as in the process of FIG. 2, and alkoxylation (k), catalyst removal (l) and distillation (m) correspond alkoxylation (h), catalyst removal (i) and distillation (j) in the process of FIG. 2, respectively. A portion or the whole of the recovered alcohol obtained by distillation is recycled (n) to either one of the steps of oxidation (a), hydrolysis (b), separation (c), saponification (d), esterification (f) and distillation (g). It is most desirable, as illustrated with respect to the process of FIG. 2, to recycle said recovered alcohol portion to the esterification step (f), the remainder of the recovered alcohol is recycled to the alkoxylation step (k). A better result is obtainable by recycling the forerun (n) to the esterification step and the other fractions (o), if necessary after drying, to the alkoxylation step (k).

In accordance with the process of FIG. 3, an alkylene oxide adduct of alcohol having uniform good quality is continuously produced from a hydrocarbon as described above without the need of careful adjustment of the alkoxylation and distillation conditions. In the process of FIG. 3 there is obtained alkylene oxide adducts which are further improved in color and odor when compared with those of the process of FIG. 2. Example IV is a specific example of the process.

EXAMPLE I

A straight chain saturated alcohol mixture of an average molecular weight of 200 consisting of $C_{12} - C_{14}$ alcohols and containing 2% by weight of impurities consisting essentially of ketones and hydrocarbons was used as a raw material. 100 kg of the alcohols and 300 g of boron trifluoride etherate were charged to a jacketed stainless steel reaction vessel equipped with a stirrer, a thermometer and an inlet pipe for liquid. The reaction vessel was then purged of air with gaseous nitrogen and its inner pressure was raised to 5 kg/cm²G. Through the liquid inlet there was introduced 38 kg of ethylene oxide into the reaction vessel over about 3 hours as to maintain a reaction temperature not exceeding 70°C, with stirring. The stirring was continued for additional 30 minutes. The reaction mixture was then neutralized with a methanolic sodium hydroxide solution, methanol and a trace of ether were distilled off and precipitated salts were removed by filteration. The reaction mixture was then distilled under reduced pressure until 50 kg of distillate was recovered to obtain as residue 88 kg of an adduct of an average added mole member ($\bar{n}$) of ethylene oxide per mole of alcohol of 3.0.

5 kg of the distillate was added with 550 g of orthoboric acid, charged in a stirred second reaction vessel and stirred at 150°C while distilling off liberated water at 300 Torr to effect esterification. The esterified mixture was then distilled at 190°C, 5 Torr, to distill off about 200 g of volatile matter, which was discarded. The residue was, after cooling, added to 5 liters of water and agitated at 90°C. The mixture was then allowed to stand still and a layer of aqueous boric acid solution was separated. This procedure was repeated 3 times to completely eliminate boric acid from the residue. The oily layer thus obtained was combined with the balance of the distillate and, after being dried under reduced pressure, recycled for esterification of the second round of operation. The operation was repeated over and over under the same operating conditions except that after the second round (1) the purity of recovered alcohol was determined by the following manner: purity of recovered alcohol (wt. %) = 100 − (impurity wt. % + combined E O wt. %) where impurity wt. % = carbonyl compounds wt. % + hydrocarbons wt. % combined E O wt. % = weight % of chemically bonded ethylene oxide unit based on the weight of recovered alcohol.

The fresh alcohol was charged together with the recovered alcohol into the first reaction vessel in a total amount as to provide 98 kg of pure alcohol constituent, (2) ethylene oxide was fed in an amount, together with the combined ethylene oxide in the recovered alcohol to be recycled, of 38 kg, (3) the quantity of the distillate drawn out of the first distillation stage was adjusted to (48 kg + $\alpha$) wherein $\alpha$ is the total weight of impurities introduced into the first reaction vessel, and (4) at all times the amount of a portion of the distillate introduced into the second reaction vessel was 10 % by weight of the total amount of the distillate.

Table I

| Round Number | 1 | 3 | 5 | 7 | 10 | 20 | 30 | 50 | 90 |
|---|---|---|---|---|---|---|---|---|---|
| $\alpha$(kg) | 2.0 | 3.5 | 4.8 | 5.7 | 6.9 | 8.3 | 8.5 | 8.6 | 8.5 |
| $\bar{n}$ | 3.0 | 3.0 | 2.9 | 3.0 | 2.9 | 3.1 | 3.0 | 3.0 | 3.0 |
| Product CV* | 0.3 | 0.3 | 0.4 | 0.3 | 0.3 | 0.3 | 0.2 | 0.3 | 0.4 |

*CV : carbonyl value (in all the tables in this specification)

As indicated by the results summarized in the above Table I, there was obtained, on and after 20th round, an alcohol ethoxylate without substantial change in the quantity of alcohol charged into the first reaction vessel and the quantity of distillate, in the distillation step while it was necessary to adjust slightly the quantity of alcohol charged in the early rounds.

COMPARATIVE EXAMPLE I

An adduct of $\bar{n}$ = 3 was obtained from the same raw alcohols as in Example I in the same process as in Example I except that the distillate, i.e. the recovered alcohol, was, after drying, directly recycled to the alkoxylation.

Table II

| Round Number | 1 | 3 | 5 | 7 | 10 | 20 | 30 | 50 | 90 |
|---|---|---|---|---|---|---|---|---|---|
| $\alpha$(kg) | 2.0 | 4.0 | 5.9 | 7.8 | 10.7 | 18 | 26 | 45 | 75 |
| $\bar{n}$ | 3.0 | 2.9 | 2.9 | 3.1 | 3.0 | 3.1 | 2.9 | 3.0 | 3.1 |
| Product CV* | 0.3 | 0.2 | 0.3 | 0.4 | 0.4 | 0.6 | 0.8 | 2.8 | 6.0 |

As indicated by the above Table II, it was necessary to adjust the quantity of alcohol charged to the first reaction vessel over a fairly wide range. Nevertheless there was not obtained a product of uniform quality as indicated by the fact that the content of impurities in the recovered alcohol did not level off and instead showed a tendency to increase infinitely and that the carbonyl value also increased gradually.

EXAMPLE II

The same alcohol as used in Example 1 was ethoxylated in the same procedure as in Example 1 and, after removal of the catalyst, subjected to distillation under reduced pressure to obtain 2 kg of forerun and 48 kg of following distillate and, as residue, 88 kg of an adduct of $\bar{n} = 3.0$. 2 kg of the forerun was charged into a small reaction vessel, admixed with 200 g of orthoboric acid, stirred at 150°C, 300 Torr, while distilling off water to effect esterification, and, after being post treated in the same manner as in Example I, combined with 48 kg of the following fraction, dried under reduced pressure and recycled for the second round operation. The operation was carried out repeatedly and after the second round, in a similar manner as in Example I except that, at all times, 2 kg of forerun was cut away and subjected to esterification with boric acid.

Table III

| Round Number | 1 | 3 | 5 | 7 | 10 | 20 | 30 | 50 | 90 |
|---|---|---|---|---|---|---|---|---|---|
| α(kg) | 2.0 | 2.6 | 3.1 | 3.6 | 4.2 | 4.6 | 4.8 | 4.8 | 4.8 |
| $\bar{n}$ | 3.0 | 2.8 | 3.0 | 3.0 | 3.0 | 3.1 | 3.0 | 2.9 | 3.0 |
| Product CV | 0.2 | 0.3 | 0.3 | 0.2 | 0.3 | 0.3 | 0.2 | 0.3 | 0.2 |

As shown in the above Table III, an alcohol ethoxylate of uniform good quality was obtained by slightly adjusting the charge of alcohols into the ethoxylation vessel and, in operation during and after the 20th round, without substantial change in the amount of charge into the first reaction vessel and the quantity of distillate.

EXAMPLE III

Using as a raw material a n-paraffin mixture of an average molecular weight of 184 having 12 to 14 carbon atoms per molecule, a process consisting of a series of steps (a) to (g), as illustrated in FIG. 2, was operated for 50 days in a completely continuous manner. In oxidation step (a) there was fed fresh n-paraffin and recovered n-paraffin at a total feed rate of 25 kg/h together with metaboric acid at a feed rate of 0.6 kg/h and oxidation with air diluted with gaseous nitrogen in the oxidation zone was carried out under the following operating conditions: residence time of 2 hours, reaction temperature of about 170°C, under normal pressure, and at conversion of n-paraffin of an average 15 %. In esterification step (b), esterification was carried out under the following conditions: residence time of 30 minutes and reaction temperature of about 170°C, while charging the forerun from distillation step (j) of recovered alcohol at a rate of 154 g/h. In distillation step (c), distillation was carried out under a pressure of 5 Torr to obtain an effluent from the bottom of the kettle at a rate of about 4 kg/h. In saponification step (d), the distillate was stirred with an amount of 20 % by weight, based on the weight of the oily layer in the distillate, of a 10 % aqueous sodium hydroxide at 100°C for a residence time of 1 hour and then recycled to oxidation step (a), after being washed with water. In hydrolysis step (e) and separation step (f), the bottom liquid from distillation step (c) was contacted countercurrently with a mixture of fresh water and a boric acid-containing mother liquor from the boron compound recovery step, the mixture being fed at a total rate of about 4 liter/hr under the following conditions: residence time of about 30 minutes, temperature of 95°C. An aqueous layer containing boric acid was fed to the boron compound recovery step, boric acid recovered therein was dehydrated into metaboric acid and recycled to oxidation step (a), and the mother liquor was recycled to hydrolysis step (e). In purification step (g), a 20 % aqueous sodium hydroxide was supplied at a feed rate to provide 10 % excess alkali over the necessary amount of alkali calculated on the basis of the saponification value of the crude alcohol and saponification was carried out with stirring at 100°C for a residence time of about 1 hour. The mixture was then contacted countercurrently with a stream of water at a feed rate of 4 liter/hr for a residence time of 20 minutes. Distillation of alcohol was then carried out in a batchwise operation and there was obtained, after removal of water and forerun, purified alcohol at a rate in average of 2.9 kg/hr. Crude alcohol obtained in continuous operation for 24 hours was distilled in one batch, and the distillation was carried out under a pressure of Torr to recover the fraction boiling in the range of from 130° to 180°C as the purified alcohol. The alcohol thus obtained was fed to ethoxylation step (h) together with the remaining fractions of recovered alcohol from distillation step (j). Step (h) to step (j) were carried out, for convenience, in a batchwise operation and there was repeated ethoxylation of about 140 kg/batch of alcohol. Accordingly, the alcohol from step (a) to step (g) was consumed in operation, one batch a day. In ethoxylation step (h), there were charged 69.5 ± 0.5 kg/batch of fresh alcohol and 70 ± 0.5 kg/batch of recovered alcohol, 400 g/batch of boron trifluoride etherate and 44.4 kg/batch of ethylene oxide. The ethoxylation and catalyst removal in step (i) were carried out in similar ways as in the corresponding steps in the process of Example I. In step (j), distillation was carried out under a pressure of 5 Torr to obtain 3.7 kg/batch of a forerun and (70 ± 0.5) kg/batch of the following fraction and, as residue, an average 110 kg/batch of an alcohol ethoxylate of $\bar{n}$ of closely 3. The forerun was recycled continuously at a rate of 154 g/hr to esterification step (b), and the balance of recovered alcohol was, after drying, recycled to step (h). The value of $\bar{n}$ and of C.V of the product after 10 days operation were 3.0 ± 0.1 and 0.2 to 0.4, respectively. The color value of the product was below A.P.H.A. 100.

EXAMPLE IV

Using the same raw paraffin as used in Example III, each operation of step (a) to step (i) in accordance with the process of FIG. 3 was carried out for 50 days in a continuous manner. Oxidation step (a) was performed in the same way as in Example III. In hydrolysis step (b) and separation step (c), the oxidation mixture from oxidation step (a) was contacted countercurrently at a residence time of about 30 minutes with a mixture of fresh water and the boric acid-containing mother liquor from boron compound recovery step the mixture being fed at a total rate of 10 liter/hr. The aqueous layer containing boric acid in a high concentration was introduced into the boron compound recovery stage in which recovered orthoboric acid was dehydrated into metaboric acid and recycled to oxidation step while the mother liquor was recycled to hydrolysis step (b). The organic layer from separation step (c) was stirred in saponification stage (d) at 100°C for a residence time of about 1 hour with a 20 % aqueous sodium hydroxide being fed at a rate to provide 10 % excess alkali over the necessary amount of alkali calculated on the basis of the saponification value of the organic layer and was then contacted countercurrently for a residence time of 20 minutes with a stream of water fed at a rate of 10 liters/hr. In esterification step (e), the effluent from state (d) was treated, together with the recycle from distillation step (m), at a temperature of 150°C under reduced pressure for a residence time of 1 hour with orthoboric acid fed at a rate of 600 g/hr, with the elimination of liberated water. In distillation step (f), the effluent from step (e) was processed in the same way as in the distillation step (c) in Example III. The distillate thus obtained was recycled directly to oxidation step (a). The residue was processed in hydrolysis step (h) and separation step (i) in the same way as in steps (e) and (f) in Example III, an aqueous layer containing a large amount of boric acid thus separated was introduced into the boric acid recovery step in which orthoboric acid was recovered. The orthoboric acid recovered was recycled to esterification step (e) and the mother liquor was recycled to hydrolysis step (b). The organic layer separated in separation step (i) was processed in distillation step (j) in the same way as in the distillation step (g) in Example III to obtain as distillate an alcohol at a rate in average of 2.9 kg/hr. Each operation in steps (k) to (m) was carried out in the same way as in steps (h) to (j) in Example III, while recycling the forerun of recovered alcohol at a rate of 154 g/hr to esterification step (e). The ethoxylate thus obtained was of similar quality with that of the product of Example III except for its color below of APHA 50.

What is claimed is:

1. In a method of manufacturing alkylene oxide adducts of an aliphatic alcohol which comprises the steps of:
    a. admixing an alkylene oxide having 2 to 4 carbon atoms with the aliphatic alcohol in the presence of an acid catalyst selected from the group consisting of sulfuric acid, phosphoric acid and Friedel-Crafts catalysts to form an addition reaction mixture and
    b. distilling said reaction mixture to obtain an alcoholic distillate and a residue consisting essentially of an alkylene oxide adduct of the aliphatic alcohol;

wherein said aliphatic alcohol is obtained by the liquid phase oxidation of a saturated aliphatic hydrocarbon having 8 to 20 carbon atoms in the presence of a boron compound by contacting with a molecular oxygen containing gas;

the improvement comprising:
    i. combining said method of manufacturing alkylene oxide adducts with a method of manufacturing the aliphatic alcohol employed in step (a) which method comprises the steps of:
        a'. subjecting a saturated aliphatic hydrocarbon having 8 to 20 carbon atoms to oxidation by contacting said hydrocarbon with a molecular oxygen-containing gas in the liquid phase in the presence of a boron compound which is capable of forming a boric acid upon contact with water to form a reaction mixture containing a borate ester,
        b'. contacting said reaction mixture with water at a temperature between 20° and 200°C to form an organic layer and an aqueous layer, the weight ratio of water to said reaction mixture being between 10:1 to 1:10,
        c'. separating said layers,
        d'. subjecting said organic layer to saponification by contacting said organic layer with an aqueous alkali metal hydroxide,
        e'. adding a compound selected from the group consisting of orthoboric acid, metaboric acid, pyroboric acid and boric acid anhydride to the saponified organic layer to convert the alcohol in said organic layer into the corresponding borate ester,
        f'. distilling the resulting mixture of step (e') to obtain a crude borate ester residue and a distillate consisting essentially of unreacted hydrocarbon and volatile by-product,
        g'. recycling said distillate to oxidation step (a'),
        h'. contacting said residue with water at a temperature between 20° to 200°C to form a second organic layer and a second aqueous layer, the weight ratio of water to said residue being between 10:1 to 1:10,
        i'. separating said layers, and
        j'. distilling said second organic layer to obtain a product consisting essentially of said aliphatic alcohol; and
    ii. cycling 1 to 50% by weight of the distillate from step (b) of the method of manufacturing the alkylene oxide adducts to any of the steps (b'), (c'), (d'), (e') or (f') of the method of manufacturing the aliphatic alcohol.

2. A method according to claim 1, wherein the average number of adduct moles of said alkylene oxide per aliphatic alcohol is between 1 and 6.

3. A method according to claim 1, wherein said acid catalyst is selected from the group consisting of boron trifluoride and boron trifluoride complexes.

4. A method according to claim 1, wherein said compound of step (e') is employed in an amount of 0.3 to 3 gram-atoms of boron atom per mole of alcohol.

5. A method according to claim 1, wherein said saturated aliphatic hydrocarbon in step (a') is at least one member selected from the group consisting of n-decane, n-undecane, n-dodecane, n-tridecane, n-tetradecane, n-pentadecane, n-hexadecane, n-heptadecane and n-octadecane.

6. A method according to claim 1, wherein 1 to 50 % by weight of said distillate from step (b) is recycled to the step (e').

7. A method according to claim 1, wherein said alkylene oxide is ethylene oxide.

8. A method according to claim 1, wherein said boron compound in step (a') is selected from the group consisting of boric acids, salts of boric acids, boric acid anhydride, borate esters and boroxines.

* * * * *